(12) United States Patent
Ebner-Todd

(10) Patent No.: US 11,315,437 B2
(45) Date of Patent: Apr. 26, 2022

(54) NUTRITION MANAGEMENT AND KITCHEN APPLIANCE

(71) Applicant: Rene Ebner-Todd, Fort Gratiot, MI (US)

(72) Inventor: Rene Ebner-Todd, Fort Gratiot, MI (US)

( * ) Notice: Subject to any disclaimer, the term of this patent is extended or adjusted under 35 U.S.C. 154(b) by 16 days.

(21) Appl. No.: 16/082,631

(22) PCT Filed: Feb. 23, 2018

(86) PCT No.: PCT/US2018/019388
§ 371 (c)(1),
(2) Date: Sep. 6, 2018

(87) PCT Pub. No.: WO2018/156875
PCT Pub. Date: Aug. 30, 2018

(65) Prior Publication Data
US 2020/0302826 A1   Sep. 24, 2020

Related U.S. Application Data

(60) Provisional application No. 62/463,282, filed on Feb. 24, 2017.

(51) Int. Cl.
*G09B 19/00* (2006.01)
*G16H 10/60* (2018.01)
(Continued)

(52) U.S. Cl.
CPC ..... *G09B 19/0092* (2013.01); *G06Q 30/0631* (2013.01); *G06Q 30/0633* (2013.01);
(Continued)

(58) Field of Classification Search
None
See application file for complete search history.

(56) References Cited

U.S. PATENT DOCUMENTS 5,260,219 A * 11/1993 Fritz ............... A61B 5/00
  435/12
2005/0080650 A1* 4/2005 Noel ............... G16H 20/60
  705/2

(Continued)

*Primary Examiner* — Nathan Hillery
(74) *Attorney, Agent, or Firm* — Kohn & Associates, PLLC

(57) ABSTRACT

A nutrition management system including a patient mobile application stored on non-transitory computer-readable media in electronic communication with a home nutrient-testing device, and a dietitian's software stored on non-transitory computer-readable media in electronic communication with the patient mobile application. A method of nutrition management, by a patient testing their nutrition levels on a home nutrient-testing device, and creating personalized daily dietary recommendations on a meal-by-meal basis for the patient based on results from the home nutrient-testing device. A kitchen device for creating hot and cold meals or drinks, including an ingredient chamber, an interface screen in electronic communication with said ingredient chamber, and an accessible preparation chamber in operable connection with said ingredient chamber and in electronic communication with the interface screen, the kitchen device being in electronic communication with a patient mobile application stored on non-transitory computer-readable media. A method of using the kitchen device.

13 Claims, 10 Drawing Sheets

(51) Int. Cl.
*G16H 20/60* (2018.01)
*G06Q 30/06* (2012.01)
*A61B 5/00* (2006.01)

(52) U.S. Cl.
CPC .............. *G16H 10/60* (2018.01); *G16H 20/60* (2018.01); *A61B 5/4866* (2013.01)

(56) References Cited

U.S. PATENT DOCUMENTS

| | | | | |
|---|---|---|---|---|
| 2005/0240434 A1* | 10/2005 | Wooten | ................. | G16H 20/60 705/2 |
| 2006/0041452 A1* | 2/2006 | Kulkarni | ................ | G16H 10/20 705/3 |
| 2006/0199155 A1* | 9/2006 | Mosher | ............. | G09B 19/0092 434/127 |
| 2010/0210541 A1* | 8/2010 | Pfuetzner | ................. | A61P 3/06 514/1.1 |
| 2010/0256196 A1* | 10/2010 | Pfuetzner | ........... | G01N 33/6893 514/342 |
| 2010/0273258 A1* | 10/2010 | Lannutti | ................ | C12M 35/08 435/366 |
| 2011/0118134 A1* | 5/2011 | Pfuetzner | ............ | G01N 33/6893 506/9 |
| 2012/0072233 A1* | 3/2012 | Hanlon | .................. | G16H 20/60 705/2 |
| 2012/0083669 A1* | 4/2012 | Abujbara | ............... | G16H 20/60 600/300 |
| 2012/0231431 A1* | 9/2012 | Angelides | .............. | G16H 50/20 434/262 |
| 2013/0035563 A1* | 2/2013 | Angelides | ............. | G06F 1/1684 600/301 |
| 2013/0065769 A1* | 3/2013 | Wong | ................ | G01N 33/57446 506/2 |
| 2013/0151266 A1* | 6/2013 | Randall | .................. | G06Q 10/10 705/2 |
| 2014/0221284 A1* | 8/2014 | Pfuetzner | .............. | G01N 33/74 514/5.9 |
| 2016/0241653 A1* | 8/2016 | Ciepiel | ................. | A47J 36/321 |
| 2016/0338953 A1* | 11/2016 | Maspoch Comamala | ................... | A61P 5/00 |
| 2016/0351072 A1* | 12/2016 | Nusbaum | ................. | G16H 20/30 |
| 2017/0027168 A1* | 2/2017 | Heath | ..................... | A61P 17/00 |
| 2017/0138965 A1* | 5/2017 | Barker | ................... | A61K 45/06 |
| 2017/0189444 A1* | 7/2017 | Ismagilov | ............... | A61K 45/06 |
| 2019/0297897 A1* | 10/2019 | Mitter | ................... | A01N 63/20 |

* cited by examiner

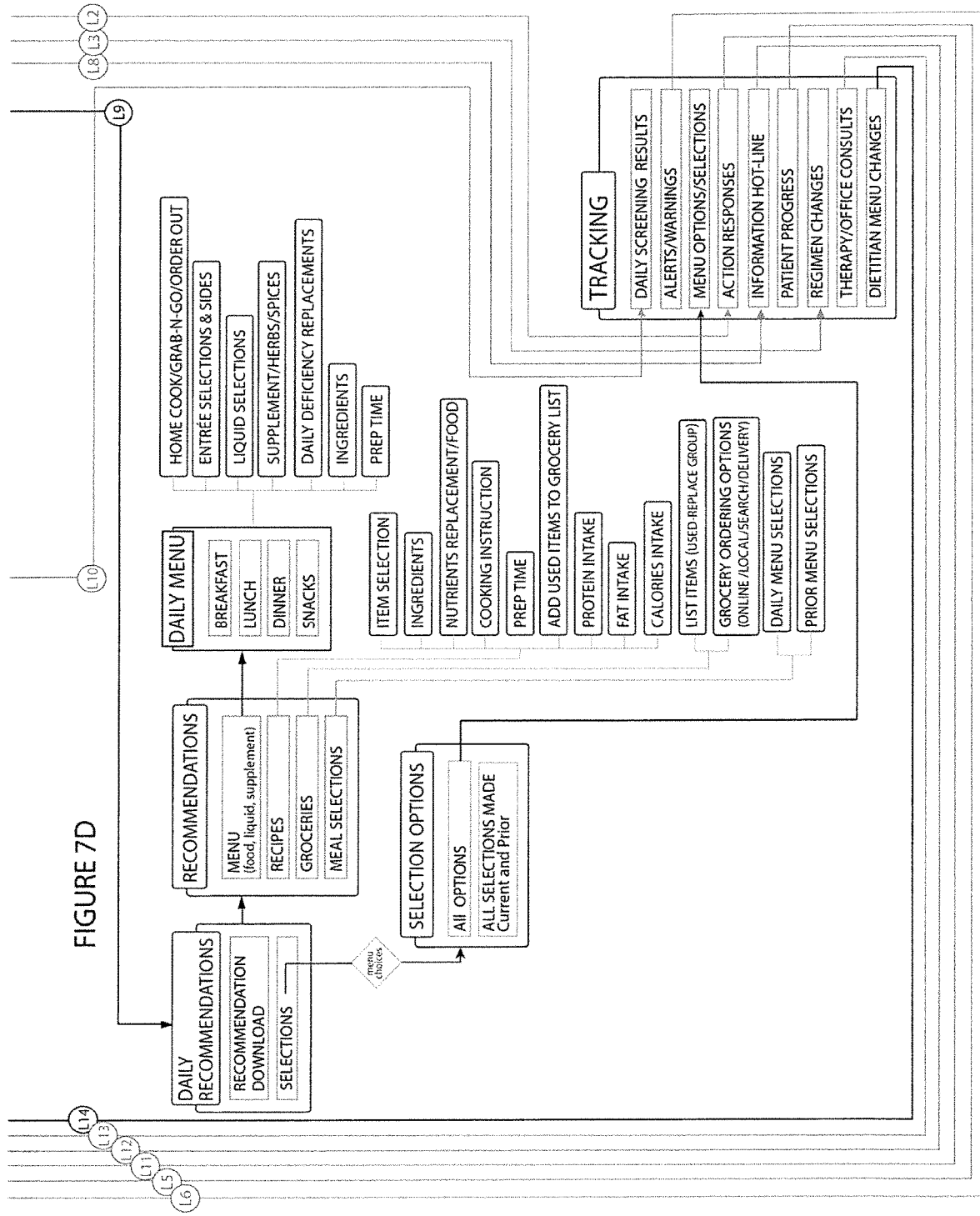

NUTRITION MANAGEMENT AND KITCHEN APPLIANCE

BACKGROUND OF THE INVENTION

1. Technical Field

The present invention relates to methods of managing nutrition. More specifically, the present invention relates to methods of managing nutrition in cancer patients and those with chronic illness or disease-associated malnutrition.

2. Background Art

World Health Organization (WHO) reported that approximately 826 million people in the world are undernourished—792 million people in the developing world and 34 million in the developed world.

Malnutrition is a broad term that can be used to describe any imbalance in nutrition; from over-nutrition often seen in the developed world, to under-nutrition seen in many developing countries, but also in hospitals and residential care facilities in developed nations. It is not necessarily caused by a lack of food, and it is not unique to poor populations, but is a common problem in patients with chronic or severe diseases.

Even in first world nations, there are malnourished people. In the United States, for example, disease associated malnutrition (DAM) affects up to 15% of ambulatory outpatients, 25%-60% of patients receiving long-term care, and 35%-65% of hospitalized patients. DAM is costly to our healthcare system and proper nutrition can lessen this cost, especially if malnutrition caused by chronic diseases is better addressed through early engagement. One potential area for dramatic cost reductions is hospital readmissions.

157 Million Americans (nearly 50% of the population) will experience at least one chronic illness in their lifetime. Persons with multiple chronic conditions may have rabid declines and a greater likelihood of long-term disability. Studies have repeatedly shown that clinical malnutrition has serious implications for recovery from disease, trauma and surgery and is generally associated with increased morbidity and mortality both in acute and chronic diseases. Contributing factors to death include a lack of sufficient nutrient testing, a lack of communication between patients and health care providers, patients' lack of understanding the warning signs of malnutrition, and confusion on the patients' part regarding strong dietary choices and individual nutrition imbalances. Maintaining healthy nutrition is also a struggle during treatment due to severe side effects that interfere with the ability to taste, swallow, cook and shop.

About 85% of Americans do not consume the US Food and Drug Administration's recommended daily intakes of the most important vitamins and minerals necessary for proper physical and mental development. When people don't get enough of the nutrients they need for good health, they run the risk of becoming malnourished.

Vitamin deficiencies are a form of malnutrition, and one vitamin deficiency in particular has become a health concern in the United States. For example: more than 75 percent of Americans are deficient in vitamin D, according to a 2009 study published in the "Archives of Internal Medicine. Eating disorders, some medical conditions, and obesity can also lead to malnourishment. Celiac disease, chronic liver disease, Cohn's disease, and some cancers can affect the body's ability to absorb sugars, fats, proteins and vitamins. Certain medications can also limit the body's ability to absorb nutrients, as can surgical procedures designed to treat obesity. Further, those who anorexic, bulimic or obese run the risk of malnutrition, because they don't get enough of the right nutrition, or that nutrition never reaches the stomach.

Patients that opt for outpatient or home treatment programs are not monitored form malnutrition therefore lack of communication between home patients and there care providers can result in valuable lost time in diagnosis of malnutrition and without proper nutrition intervention patients conditions can deteriorate too rapidly making it too difficult to change their outcomes.

Currently, there are no daily home deficiency monitoring systems that offer daily nutrient testing for patients. Patients or their caregivers are responsible for tracking their own dietary intake and a patient's physician orders dietary assistance on a case-by-case basis.

Post hospital care is provided to the patients at the time of discharge as sell as care doctor ordered care instructions. Dietary pamphlets, written instructions, and information about online resources or additional dietary services are provided to patients and caregivers to further manage their dietary needs. Additional dietary services or private dietary care specialists require that patient's track their own dietary intake and daily fitness in addition to their consulting services, but these are not tailored to a particular patient's medical needs or daily symptom changes. Also, research has confirmed that 65%-80% of patients take vitamin supplements without the authorization or knowledge of their care providers, which, can worsen treatment side effects or cause negative medication interactions.

Some food production and health fitness monitoring systems do exist, but they do not provide the recommendations based on full nutrient testing and coordination with food production.

One currently available system is described in US Patent Application Publication No. 20170226661 to Sundaram, which discloses a method and system for providing an integrated cooking machine (shown in FIG. 1), which automates the process of cooking completely. The system includes electro-mechanical components for performing the cooking operation, which is driven by electronic circuits fed by programs. The programs are stored in the device or downloaded from the cloud platform, which authenticates these machines and provide the required information. The system also has intuitive interface on the device to create recipes. The system is also configured to measure the output parameters of the food. The system can reorder ingredients in cartridges when they run out. The user can select a recipe from their phone or the machine itself. The machine can receive data from various wearable devices (e.g. blood pressure, etc.) to aid in selection of food items. Sundaram does not disclose actually monitoring nutrition of a patient.

US Patent Application Publication No. 20170124276 to Tee discloses a mobile application for monitoring and management of users or patients with various health or disease conditions. Software system provides a platform with which the medical histories, the recent conditions and real-time measurement data for the patient can be organized and shared among various people who are involved in the caring of the patient. Diet requirements can be shared among the group. A diet program with different menus can be used by a prediabetic user. While Tee discloses monitoring a patient with sensors, there is no disclosure of monitoring their nutrition with a home nutrient-testing device.

US Patent Application Publication No. 20090234839 to Angeli, et al. discloses a computer implemented method, apparatus, and computer program product for selection of meal plans. A set of prospective guests are identified from at least one of a set of sensors collecting historical attendance data and a calendaring application. A set of nutritional requirements is then identified for the set of prospective guests. Thereafter, a set of meal plans is selected on an availability of ingredients and the nutritional requirements of the set of prospective guests, wherein the availability of ingredients is determined by sensors from the set of sensors monitoring the ingredients. While nutritional requirements can be entered into the program, Angeli, et al. does not disclose monitoring user's nutrition or communicating their nutrition to dietitians. Angeli, et al. further does not disclose a kitchen device that makes meals related to the selected meal plans.

There are many drawbacks to these current methods of providing cancer patients with nutrition. Most generally, malnutrition is not being diagnosed early enough to save lives. Poor dietary practices often mask malnutrition symptoms, causing this condition to be misdiagnosed. Further, inaccurate testing results occur when deficiencies are not tested daily. In rare instances when deficiency testing is ordered for a patient, the testing usually comes in response to a patient's severe weight loss; when deficiencies are detected at this point, dieticians might be brought into the treatment process, but by then it will be too late to save the patient's life. Further compounding the issue is the fact that doctors are not trained in nutrition, which results in a lack of doctor/patient dialog about nutrition practices. This lack of dialog creates patient confusion regarding appropriate dietary choices. Other problematic nutrition issues include the difficulty of ensuring patients' compliance with their assigned nutrition programs once they return home after hospital treatment. Additionally, dietary intake provided by the patients is unreliable and often incomplete. Moreover, pamphlets providing dietary information are often difficult for patients to understand, patients have difficulty knowing which online resource information to trust when it comes to nutrition assistance, and improper vitamin supplement usage can cause dangerous interactions with treatment medications and worsen or prolong side effects.

In a dietary program, ease of use is a critical factor. Patients and caregivers would like quick and accurate information, and simple recommendations that provide them with the resources to make correct nutrition choices. Dietitians express that the ideal system (a system that would be most beneficial in allowing them to treat their patients) would offer flexibility, efficiency, and tracking of patients' medical information and nutrition choices, and which provides them with accurate information. For dietitians, the second most important factor in aiding patients in managing their care is patient compliance with their nutrition program. Patients affirm that over the long term, it is difficult to remain compliant with a restricted dietary program. However, research reveals that low compliance has less to do with lack of desire on a patient's part, and that better compliance can be achieved with readily available support, and by providing clarity about how nutrients relate to dietary plans, and thus aid in eventual recovery.

There remains a need for daily testing of nutrient deficiencies in disease-associated malnutrition and cancer patients, daily professional dietary assistance, data management that tracks patient nutrient progress, and tangible solutions in the form of personalized recommendations for meal selections.

SUMMARY OF THE INVENTION

The present invention provides for a nutrition management system including a patient mobile application stored on non-transitory computer-readable media in electronic communication with a home nutrient-testing device, and a dietitian's software stored on non-transitory computer-readable media in electronic communication with said patient mobile application.

The present invention provides for a method of nutrition management, by a patient testing their nutrition levels on a home nutrient-testing device, creating personalized daily dietary recommendations on a meal-by-meal basis for the patient based on results from the home nutrient-testing device, and the patient eating meals based on the recommendations.

The present invention provides for a kitchen device for creating hot and cold meals or drinks, including an ingredient chamber, an interface screen in electronic communication with said ingredient chamber, and an accessible preparation chamber in operable connection with said ingredient chamber and in electronic communication with said interface screen, the kitchen device being in electronic communication with a patient mobile application stored on non-transitory computer-readable media.

The present invention provides for a method of using the kitchen device by communicating with a patient mobile application including menus and determining available items, selecting an available item, and preparing the meal or drink within a preparation chamber.

The present invention further provides for a method of metabolic recovery of a patient through alteration of their diet, by inputting patient nutrition levels into patient software, controlling the patient's diet by dietitian's software, producing meals based on the diet.

DESCRIPTION OF THE DRAWINGS

Other advantages of the present invention are readily appreciated as the same becomes better understood by reference to the following detailed description when considered in connection with the accompanying drawings wherein:

FIG. 7A, FIG. 7B, FIG. 7C, and FIG. 7D are flowcharts of system architecture of the nutrition management system of the present invention.

DETAILED DESCRIPTION OF THE INVENTION

Figure 1:
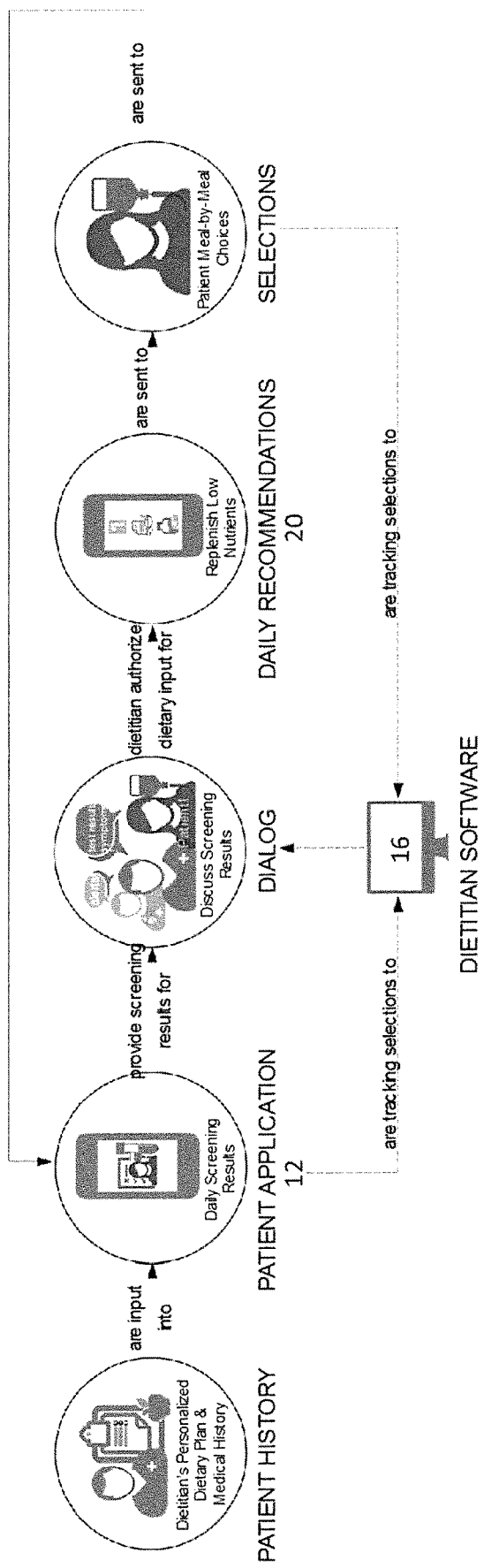
FIG. 1 is the system architecture for the present invention.

The present invention generally provides for a nutrition management system 10 for use by cancer patients, patients with disease-associated malnutrition, and others with chronic illness (such as those with food restrictions/limitations/specialized diets), or by any health conscious individual, with the system architecture shown in FIG. 1. The system 10 includes a patient mobile application 12 and a home nutrient-testing device 14 in electronic communication (either wired or wireless). The patient mobile application 12 is further in electronic communication with a dietitian's software 16.

Most generally, the present invention provides for a method of metabolic recovery of a patient through alteration of their diet, by inputting patient nutrition levels into patient software (i.e. the patient mobile application 12), controlling the patient's diet by dietitian's software (dietitian's software 16), and producing meals based on the diet (with a kitchen device 40). In other words, the software in the present invention is an interface between the patient's medical condition and metabolic disorder produced by their condition/disease/treatment (such as chemotherapy and/or radiation in the instance of cancer, the flu, or any other condition) and the patient's metabolic recovery through the monitoring and alteration of their diet with the assistance of the dietitian with the production of meals based on the diet. The technical effect of the software is the metabolic recovery of the patient through the recommended meals that the patient then eats. It should be understood that while the home nutrient-testing device 14 can be used to update the patient's nutrition levels into the patient mobile application 12, the information can also be updated manually from tests or medical records daily or as needed.

The term "application" as used herein refers to a computer software application, otherwise known as an "app", that is run and operated on a mobile device, such as, but not limited to, smart phones (IPHONE® (Apple, Inc.), ANDROID™ devices (Google, Inc.), WINDOWS® devices (Microsoft)), mp3 players (IPOD TOUCH® (Apple, Inc.)), or tablet computers (IPAD® (Apple, Inc.)), especially ones utilizing a touch screen. The applications herein are stored on non-transitory computer readable media.

The system is introduced immediately after a patient's diagnosis and can follow the patient through survivorship (FIG. 1). By engaging cancer patients, disease-associated malnutrition patients, and chronic illness patients early after their diagnosis, their risk of death due to malnutrition can be lowered and their quality of life can be improved throughout their treatment and beyond. Additionally, as patients home-test for nutrient deficiencies on a daily basis, this can initiate conversations between patients and healthcare providers.

First, based on a patient's medical history and habits, a registered dietitian works with the patient's oncology team to create a first set of specific menus unique to each patient (for breakfast, lunch, dinner, snacks, drinks, dessert, and combinations thereof). The menus can include recipes for any items such as hot meals and cold meals (soups, stews, broths, fruits, grains, pasta, rice, etc.) and drinks (smoothies, herbal teas, juices). The menus and all associated information are then input into the patient's mobile application 12 and the dietitian's software 16 used during the analysis process and thus provides the technical effect of accurate personalized care. The patient then can use the system 10 at home.

Figure 2:
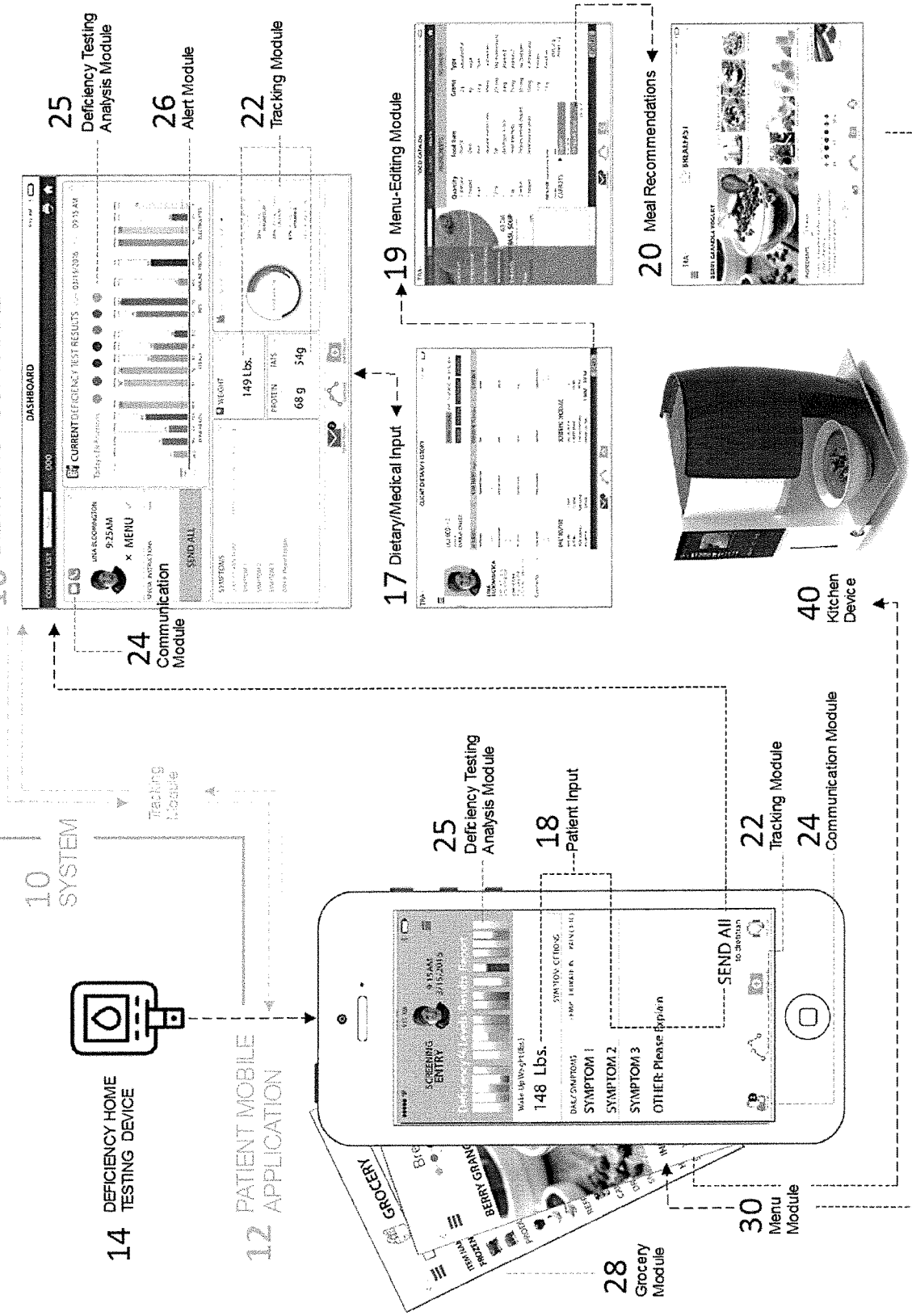
FIG. 2 is a depiction of the nutrition management system of the present invention.

Because nutrients change daily, patients must test their nutrition levels every day with the home nutrient-testing device 14 provided that connects to the patient's mobile application 12 (FIG. 2). The home nutrient-testing device 14 measures nutrient levels in the body daily for the nutrient necessary to achieve nutritional balance and absorption to maintain optimal health, such as nutrients for bone growth (vitamin D, magnesium, calcium, vitamin A, vitamin K), nutrients for metabolism (vitamin B complex (B1, B2, B3, B5, B6, B12), fats (omega-3, omega-6), nutrients for protein absorption (vitamin E), nutrients for the immune system (vitamin C), and electrolytes (sodium, chloride, zinc, potassium, $HPO_{42}$ Phosphate).

The home nutrient-testing device 14 is a portable nano-scale microscope programmed to detect nutrient levels found in an individuals bodily fluids. Test strips are provided to collect the samples and fit into a cartridge that inserts into the home nutrient-testing device. Once testing is performed, the data analysis module 25 automatically inputs the results into the patient's mobile application 12. The patient mobile application 12 also prompts the patient to input 18 daily symptoms and morning weight immediately following the testing. Patients generally test in the mornings, but for those patients who work afternoons, nights, or swing shifts, their testing times can be varied based on baseline testing.

Currently, it takes more than one method to test all of an individual's nutrients (macro and micro) in order to complete full nutrition assessments. Doctors rely on a series of blood testing results of macronutrient levels and rapid changes in weight as determinants of malabsorption. Macronutrients are tested separately and manually input into the medical and dietary history Inputs 17. Both micronutrients from the home nutrient-testing device 14 and the macronutrients inputs set the limits for the algorithm data searches use to determine the activation setting for the alert module 26 and the personalized menu creation module 19.

Based on the testing and screening results 25, only menu recommendations 20 will appear as selection options for the patient/users that match the specifications set by the dietitian's data inputs. Once a selection is made from the recommendation list 20, users can either choose to prepare/cook the item by downloading the recipes 30 or send their selection to the kitchen device 40 and the appliance will prepare the hot or cold food item. There is a technical effect of providing menu recommendations 20 based on the nutritional needs of the patient at that particular moment in time, and then preparing the selections with the kitchen device 40.

Iron is an essential mineral that when low can result in anemia and is a contributing factor for malnutrition. Since iron is mineral that is slowly increase over time (2-6 months) testing once or twice a year is sufficient.

If such patients have deficiencies (such as vitamin D) that take several months to correct, their morning meals can be predetermined and consults with dietitians can be scheduled at an alternate time. Additionally, dietitians' schedules also benefit by spreading testing times throughout the day.

The home nutrient-testing device 14 only tracks micro and macro nutrients and through its data selection process it produces a list of recommendations 20 based on the set values determined by the dietitian's assessment inputs.

There are no other sensors that evaluate nutrient levels, only manual inputs from food code bar readings such as "my fitness pal" and food photo mobile applications. Some food prep programs like the Gathered Table and Forks Over Knives also use FDA labeling codes for their menu and diets selections but the diets are generalized for healthy living not medical or symptom specific and they do not test nutrient level for deficiencies. Other testing sources are lab ordered blood tests from a doctor/physician with, depending on the resource, labs in hospitals inpatients take 12 to 24 hours and the reports go directly to your doctor. Outpatient testing is sent to a lab and can take 3-5 days to get the results, online mail in testing can take 3-4 days to get the test to mail in and they take 12-48 hours to receive the testing results online. Or one can go to their local pharmacy and pick up a blood testing kit and mail it in to shorten that timeline to 24-48 hours depending on the overnight shipping arrangements. In all of theses cases by the time the patient gets the testing results their nutrient levels have changed. In situations that are not closely monitoring for water soluble intake this would be adequate, nevertheless for the cost of these kits will run on average from $300 to $1000 per test, depending on the nutrient groups the individual is testing (1-all 30 nutrients).

The patient mobile application 12 sends the results of the home nutrient-testing device 14 and patient inputs 18 to the dietitian's software 16 (mobile application). Based on this information, the dietitian uses a menu-editing module 19 that can update or adjust recommendations 20 for daily meal selections and ingredients, and send the updated recommendations 20 to the patient mobile application 12. The recommendations 20 can include menus, recipes, and supplements personalized to replenish each patient's specific daily nutrient needs for each specific meal. This provides a technical effect of updating and adjusting the recommendations 20 based on the nutrient results.

The patient mobile application 12 includes a grocery module 28. The grocery module 28 can generate grocery lists for any of the menus sent by the dietitian, and can track which ingredients or foods that have been used and determine their replacements. For patients with physical limitations or those lacking access to healthy resources, the grocery module 28 can also include access to online resources for grocery shopping and delivery services that are linked (such as Amazon FRESH®, INSTACART®, FRESH DIRECT®, or POSTMATES®).

The patient mobile application 12 can also include a menu module 30. Within the menu module 30, menus for each meal category (breakfast, lunch, dinner, snacks, drinks, dessert) can be selected based on the patient's schedule. Caregivers or individuals with limited time can personalize selections based on length of preparation time. Options include: 5-minute grab-and-go, 10-20 minute home cook, or a meal can be selected from an order-out healthy restaurant locator including "do" and "don't" recommendations. The grab-and-go option is designed to aid patients that are participation in home or out patient treatments programs but still maintain an active lifestyle, or patient with limited mobility and don't have the ability to stand and prepare their own meals. The foods in the menus are higher in nutrient content therefore a smaller portions can provided the same or higher nutrient content and freeze dried and dehydrated foods have a much longer shelf life that standard produce reducing shopping trips for those whom are struggling. Patients or caregivers will no longer have to fret over meals if they have to make an alteration to the daily selection; they can simply cancel the selection from the meal list, and a tracking module 22 can adjust the daily intake report. The effect of missing the meal selection can show up in the patient's next day's testing, however, the system 10 can adjust for that change and the event can easily be explained in the next day's consult. This flexibility is constructed into the system to reduce anxiety and promote compliance.

Figure 5:
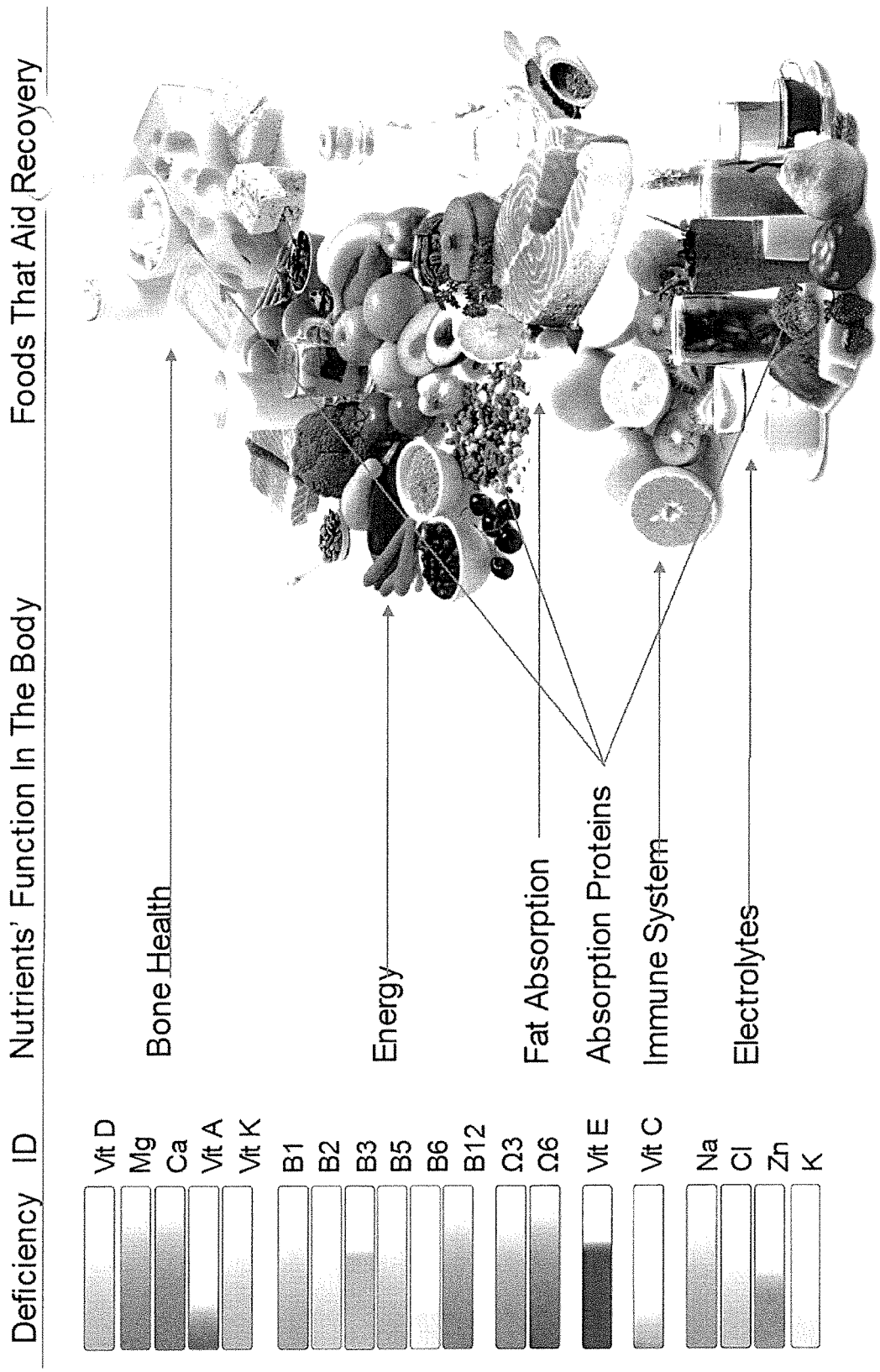
FIG. 5 is a depiction of color-coded nutrients and representative foods.

Investigative studies on the relationships between nutrients and the functions they perform in the body led to the development of a color-coding system that groups deficiencies by their functions in the body, and the foods that provide a resource for cellular rejuvenation (as shown in FIG. 5). Each deficiency color has been paired with a precisely chosen ingredient in the recipes or food sources to provide accurate replenishment based on recommended daily allowances set by the National Institute of Health. The system 10 can provide food selections necessary for each patient based on their initial input history. In addition to tracking deficiencies, the system 10 can also trace proteins, fat intake, calories and rapid fluctuations in weight, by tracking a patient's menu selections and ingredients. These are all indicators that doctors watch to detect absorption problems that can lead to malnutrition. Additionally, many treatment side effects that patients experience are in fact the result of high deficiencies, and can be resolved through the correct dietary intake that restores balance to the body. Because too many of some nutrients can be as harmful as too few, the system 10 searches for selections that will achieve nutrient balance by the end of each day. Meal selections and menus change in real time throughout the day as the patient makes food choices. In other words, the system 10 provides real time recommendations based on what the patient ate earlier through tracking their meal and menu selections, and the recommendations are made in order to provide the patient with the nutrients that they need for that day. If a patient made a particular menu or meal choice that did not include enough nutrients (for example, if they decided to eat out at a restaurant), the system 10 can reroute the patient back to meals with the nutrients they need for that day.

The system 10 also includes a tracking module 22 within the patient mobile application 12 that sends the patient's daily screening results and a menu selection to the dietitians' software 16 for the dietitian to use during consults with the patient. The dietitian's software 16 includes any necessary graphics in order to view the results from the deficiency testing analysis module 25, screening inputs 18, and menu selections on a mobile device screen. The tracking module 22 can provide any comparisons with the data or reports as necessary. For example, week-to-week comparisons provide dietitians additional data research on patient-to-patient similarities that can be used to improve overall quality of care. The tracking module 22 provides the technical effect of monitoring the patient's nutrition over time.

The system 10 can also include a communication module 24 that can send patients' dietary progress to medical professionals such as physicians, healthcare providers, or oncology teams.

The system 10 can include access to a dietary hotline for patients to call with quick questions, and which provides responses. The system 10 and the patient mobile application 12 can also provide an alert module 26 that sends alerts or warnings to the dietitian's software 16 or to an alternate healthcare provider in case any problems arise. This allows healthcare providers to react in a proactive way. This often eliminates unnecessary office visits or hospital readmissions.

The system 10 can also include alerts within the patient mobile application 12 for reminders to eat meals or take prescription medications at particular times, which can be set by the patient, dietitian, or medical professional. One of the hardest parts of prescription drug maintenance is compliance. The system 10 can include recommendations 20 to the patient of actions to take if a medication is missed, and can analyze interactions of the medication with foods to make sure that the patient does not choose a harmful meal selection when taking medication (for example, some medications cannot be taken with citrus juices).

Figure 4:
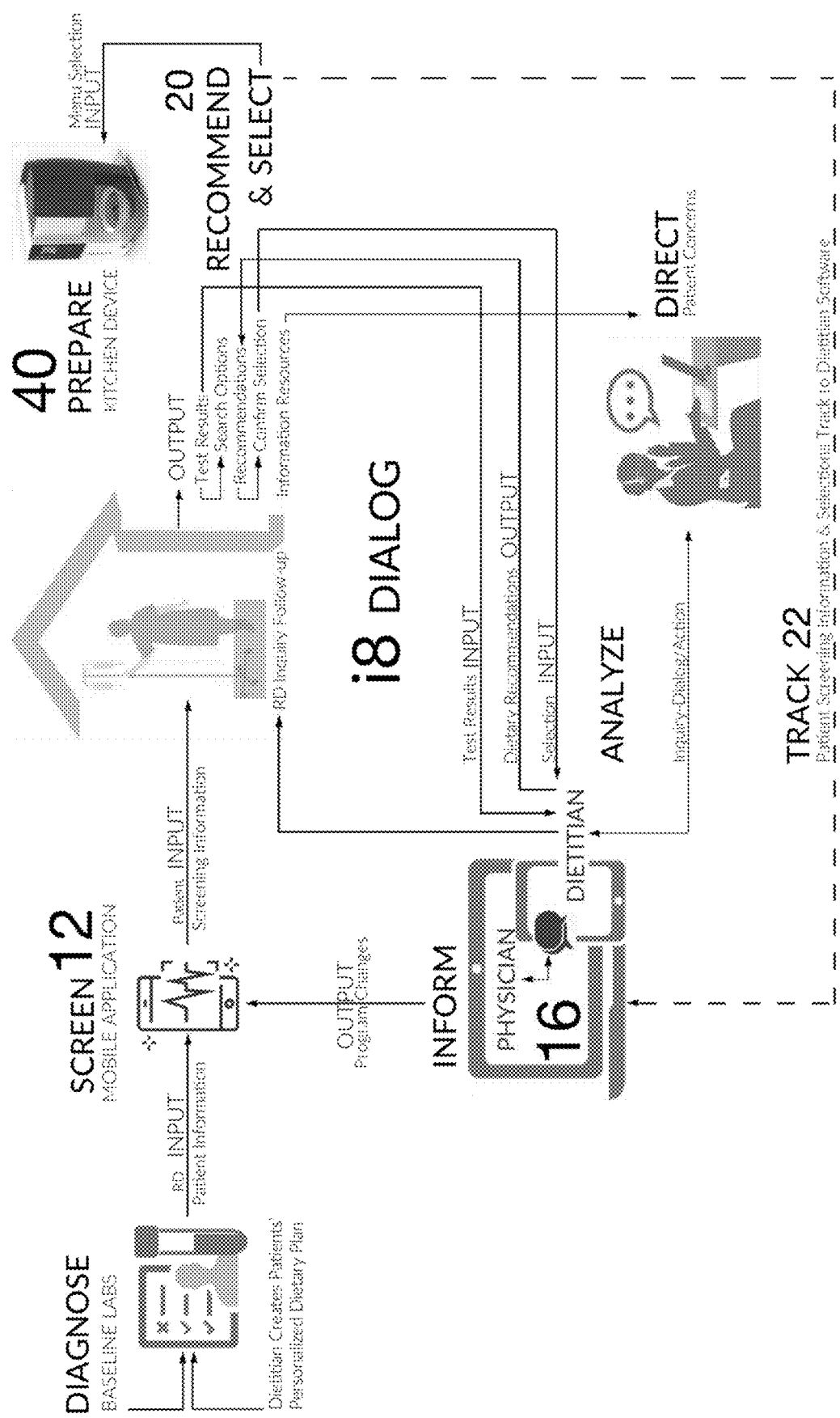
FIG. 4 is a flowchart of information in the present invention.

FIG. 4 further details the system's 10 architecture and the flow of information. FIGS. 7A-7D also illustrate this information further in flowcharts with options for selections at each step of the process (information flows between FIGURES at lines designated L1, L2, etc.). At the diagnosis or beginning of using the system 10, baseline measurements of the patient can be gathered by a laboratory and can be input into the patient mobile application 12 by the registered dietitian. Information from medical records can also be gathered by a laboratory and input into the patient mobile application 12 by the registered dietitian, such as patient history (pre-existing conditions, nutrition assessment evaluation, and preferences (likes and dislikes)), risk factors (smoking, obesity, alcohol use, and allergies), pharmaceutical history (lists of medications and treatments, drug interactions, food interactions, supplement interactions, temperature restrictions, side effects, warning instructions, and daily medication usage), medical team information (treatment schedule, and medication regimen including deficiency baseline, proteins, fats, electrolytes, white blood cell counts, and weight), and dietitian team information (dietary program information, menus/recipes such as Qüre Nutrition Science or specialized menus, and national listings (AICR/NIH)).

A dietitian can create a personalized dietary plan based on the patient's full medical records provided by the patients primary physician, nutrition assessments and dietary history conducted by a registered dietitian, current symptoms the patient is experiencing, as well as their likes/dislikes, and additional vises/habits (good and bad) that will effect daily recommendation provided to patients while participating in the nutrition management program. The aforementioned information is coded and linked to the search engines and provide the data input limits use to determine the patient's daily personalized food and menu recommendations, where as the system will provide patients with a list of selections for these recommendations 20 based on the input data provided. These inputs are loaded into both the dietitian's software 16 and the patient mobile application 12 and set the parameters for the algorithm search analysis to take place. The algorithms search for recommendations offerings (food, menus, recipe, supplements) that match the dietitian's input qualifications.

At a screening step, screening information can be entered daily in the patient mobile application 12, such as weight and symptoms by the patient. The patient is prompted daily to input their screening information and send it to the dietitian's software 16, after which, the inputs to the dietitian's software 16 can be used to conduct a pre-scheduled consults or allow for the dietitian to make manual changes to the patients dietary recommendation/selection 20 list based on their determination of the screening results data.

An output can be produced and displayed on the patient mobile application 12. Test results from the home nutrient-testing device 14 can be sent to the dietitian's software 16. The test results can also influence search options available to the patient and recommendations 20, and once the patient confirms a selection, this information is sent to the dietitian's software 16.

With the tracking module 22 analyzing deficiency and selections with the patient mobile application 12, nutrient analysis information (updating changes to program regimen, alerting dangerous levels that can be sent to professionals, collating progress and making weekly comparisons), menu selections (compliance and updating dietary changes), and case comparisons can be tracked. Alert systems embedded in the software that can identify dangerous screening data which is determined by the limits set by the dietitian when patient data is first input into the system. Therefore, any irregularities that exceed these limits automatically send a warning notification, prompting the dietitian to take immediate action, contact the patients' physician, or change the recommendations to include special instructions. If the system detects a patient has become noncompliant of a set duration of time it will also alert the dietitian to respond allowing for early engagement to help resolve the patient concerns.

Nutrient levels are determined by the dietitian at the start of the program and set in accordance with protocol the physician/healthcare team in charge of the patient treatment regimen has requested, or the patient themselves has requested prior to care. For example, if a dietitian is trying to correct absorption of vitamin D or strengthen the immune system prior to surgery, they can adjust the levels of the individual nutrients desired to stabilizes the patients balances based on their deficiencies tests to aid in correcting the deficiency or increase vitamin absorption. The same is true for foods and medication interactions, if a medication prescribed to a patients is not responding effectively for one particular patient, it may be determined that a change in that individuals diet is all that is required to aid enhance the medications effectiveness, especially in medications that are necessary to the treatment success of the patient.

With the recommendations 20, meal-by-meal daily menus can be recommended to the patient and selected by the patient, such as by Qüre Team Nutrition Scientists/professional chefs, American Cancer Institute, Great American Plate Challenge, American Institute of Cancer Research (AICR), Meal to Heal, LiveStrong Foundation, Heal Well "A Cancer Nutrition Guide", Institution Dietary Menu, or Dietitian Specialized Recipes. Daily supplements can also be recommended and selected, such as by Orthomolecular MD, Metabolic Medical Center, nutrition specialists, oncologists, registered dietitians, research and usage information data, Memorial Sloan Kettering, University Academic Studies, food interactions, or clinical studies. Recommendations 20 are set to change every day in order to assure that the patient is getting a variety of nutrients in their diet throughout the week that match the treatment regimen. Every time a patient makes a selection from the food and menu recommendation list, these selections are linked to a tracking system that calculates specific nutrient for each item regardless of whether it is a single food item, several items in a recipe or a supplement/herb/spice. If the patient/user decides to changes a food selection or skips a meal selection, the algorithms are programmed to recalculate the menu options to accommodate for the increase/decrease nutrients the individual has replaced or manually input from an alternate resource (restaurant, vending machine, etc.) for the next meal recommendation. Therefore, selection changes will not affect the patient's long-term goals. The day's selections for each patient are updated at the end of the day on the dietitian's software database. The patient's menu selection is then input into the kitchen device 40 so that the meal can be prepared.

Each selected item is automatically added to a grocery list within the grocery module 28 for easy replacement. Additional search engines can match the delivery services that best fit the patient profile. The patient can select the icon of the service or select the associated link and it can connect them with the service partner associated with the management program deliveries (Amazon Pantry, Uber, Instacart, Kroger, etc.).

The patient mobile application 12 can also output and display information resources, such as online services for inquiries. The online services can include providing a speech recognition personal assistant for researching information and "Ask a Dietitian", scheduling appointments and scheduling office visits, and secured virtual conferencing for dietary consults. As the patient moves through their day, they can see the nutrient goals increase on a health reports page which includes real time updates as nutrients are replenished as well as showing the long term progress of specified goals. Patients can also select the nutrients listed for each food, spice, herb, supplement, or a combination of all in the recipes and a reference can be provided such as to the benefit or study that was used to determine the reason for inclusion of that food or ingredient in their recommendation list. The patient can click on the item, for example, pumpkin or the vitamin color or on the recipe and it can link to the resource information. For example: Vitamin A—pumpkins are low in calories, virtually fat free & packed with potassium, vitamin A, dietary fiber, and cancer-fighting beta-carotene. Or the patient can look up the nutrient and get a list of links to general information about the deficiencies. For example, for Zinc—Zinc plays an indispensable role in creating and balancing an effective defense against infection, and low levels are linked to higher rates of various diseases. More importantly, zinc deficiencies needn't be massive in order to affect health; according to one recent study, even minor zinc deficiency can cause damage to cell DNA.

The dietitian's software 16 can include protocol for inputting patient medical history, creating dietary program, Qüre supplies input for recipes, call center follow-ups, tracing patient selections and test results, updating menus and requested changes, client consults and reviewing progress, updating medical team for patient progress. The dietitian's software 16 can analyze with an inquiry-dialog or action. The dietitian's software 16 can communicate with physicians, and physician's protocol can include MD authorize nutrition assessment or screening, and MD authorize regiment changes. The dietitian's software 16 and the physician can output to the patient mobile application 12 authorized dietary changes.

The invention provides for a method of nutrition management. Most generally, this method can include a patient testing their nutrition levels on a home nutrient-testing device, creating personalized daily dietary recommendations on a meal-by-meal basis for the patient based on results from the home nutrient-testing device, and the patient eating meals based on the recommendations. In other words, by using the system 10 of the present invention, meal recommendations can be made based on the patient's nutrition levels on a particular day and the system 10 has a technical and physical effect of the patient eating a specifically recommended meal to enhance their nutrition. More specifically, the method can include creating a menu for a patient, inputting the menu into a patient mobile application, testing nutrition levels of the patient at home, sending nutrition levels of the patient to a dietitian mobile application, and updating recommendations for the patient and sending the updated recommendations to the patient mobile application. This method can be repeated daily to adjust recommendations based on the daily nutrition levels of the patient (FIG. 1).

Figure 3:
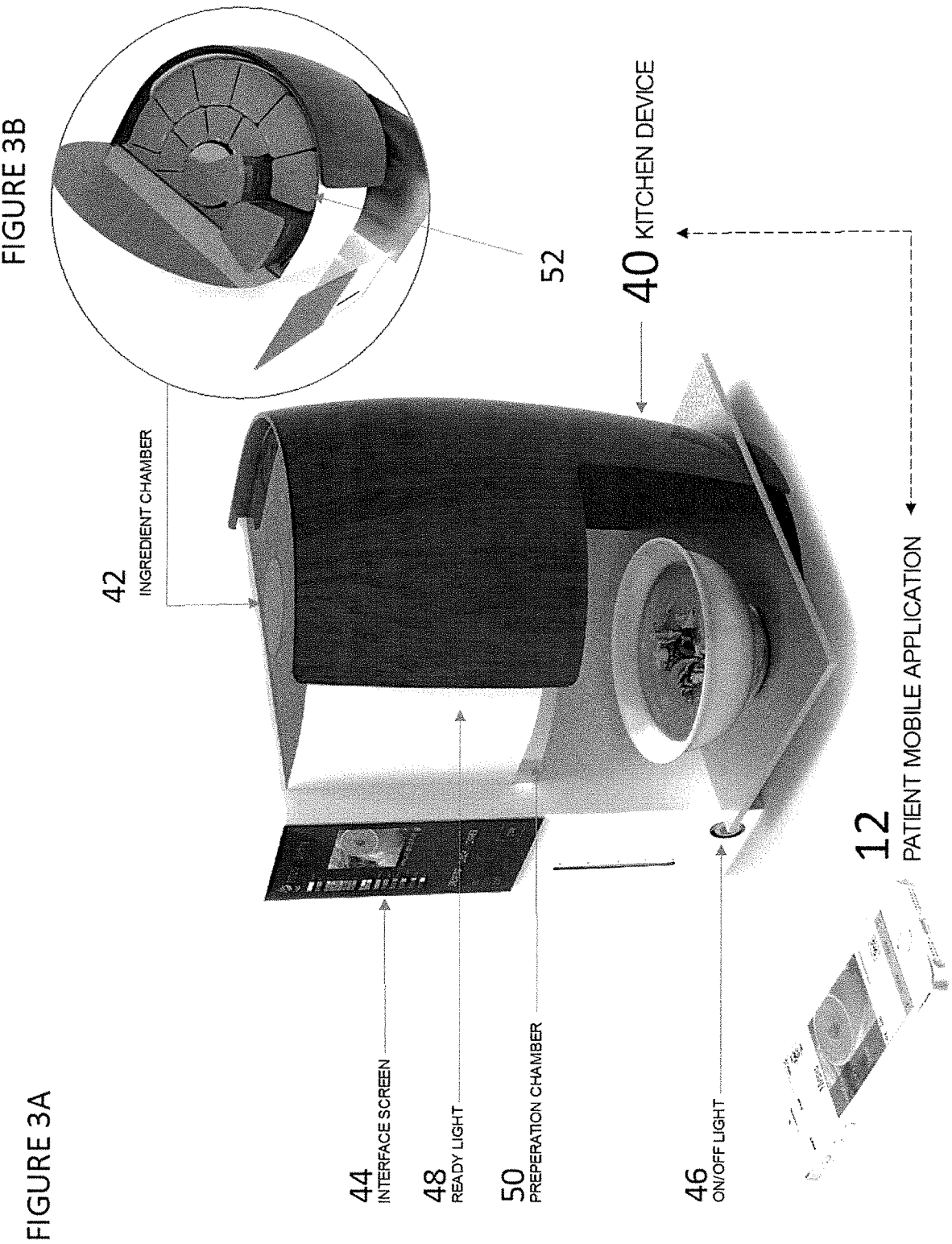
FIG. 3A is a perspective view of a kitchen device of the present invention.
FIG. 3B is a top perspective view of an ingredient chamber.

The system 10 can also be in electronic connection (wireless or wired) with a kitchen device 40 that is able to create hot and cold meals or drinks based on recipes provided by the patient mobile application 12, including an ingredient chamber 42, an interface screen 44, and an accessible preparation chamber 50 in connection with the ingredient chamber 42 (shown in FIGS. 3A and 3B). The interface screen 44 is in electronic communication with the ingredient chamber 42 and the accessible preparation chamber 50.

For patients that are unable to or do not wish to cook their own meals, the patient mobile application 12 offers the meal selections for home cooking, grab-and-go, and order out. Grab-and-go refers to the kitchen device 40 that works in conjunction with the patient mobile application 12. Data for the grab-and-go selections are managed the same as if a user was cooking the meal themselves or grabbing a single food for a snack. It is however limited to recipe selections that are able to be prepared in the kitchen device, hot/cold/add spices. The hot items can be meals (stews, soups, pasta, etc.), drinks (spice & herb teas/broths), or cold items (smoothies, juice, infused water), dry ingredients added to a food like nuts and spices combinations to an oatmeal or yogurt.

Recipe ingredients 52 (shown in cartridges 52) can be matched with freeze-dried and dehydrated ingredients, and dried herbs and spices in an ingredient chamber 42 (FIG. 3B) within the kitchen device 40. Freeze-dried and dehydrated foods chosen at the peak of freshness contain higher levels of nutrients per item than fresh foods, and have a longer shelf life because of their processing methods and vacuum sealed packaging. Any ingredients 52 can be ordered and shipped directly to the patient's home. There are preferably 18 vacuum-sealed cartridges 52 that rotate on a circular track. Each is bar coded with the contents (ingredient/food) and has a data chip for precise measurement of each ingredient 52 to produce the meal/drink item selected from the patient mobile application 12. The kitchen device 40 utilizes an authorization code to activate the menu selection and food preparation. Every item made with the kitchen device 40 tracks the exact nutrients back to the dietitian's software 16. If multiple individuals use the system in one household, to avoid confusion the system can prompt the user to change the login to identify alternate users (family, caregivers) but it can still calculate the ingredient usage to the grocery replacement list to assure that the patient/user (intended user) has the food resources available for program selections.

The cartridges 52 are sold separately and organized to prepare food selections based on the dietitian requirements as well as the user needs such as: specific to breakfast for working patients to give patients more variety in the meal selections they would utilize the most to provide more variety in one meal category. The cartridges are preferably refillable and not disposable. Dehydrated and freeze dried foods that are sealed will last in dry storage or refrigerated for up to 100 days and are higher in nutrients than fresh groceries because they are picked at the peak of freshness, free of containment's and preservatives and available in a wide variety of food options.

The kitchen device 40 can also electronically communicate with the patient mobile application 12, about which ingredients 52 are available, and thus which menus/recipes/items are available to the patient. The menu selections can be limited to simple recipes and 1-8 items. The patient can then select an available menu item (such as a grab-and-go item). Once a selection is made, it appears on an interface screen 44, as well as a screen of the patient mobile application 12, to allow for meal preparation. If an ingredient 52 is missing from the ingredient chamber 42, the kitchen device 40 can alert the patient to change cartridges/ingredients 52. If the patient does not have an ingredient 52, the patient then has an option to search for an alternative item or decline the item, as well as order a replacement for the missing ingredient. Once the selections and preparation process are complete, the kitchen device 40 measures the ingredients 52, adds water to the ingredients 52, mixes the ingredients 52, or blends the ingredients 52 (or combinations thereof) in order to prepare the recipe in the preparation chamber 50. The kitchen device 40 includes all necessary preparation hardware to perform these steps. As the kitchen device 40 is preparing the recipe, a light 46 can appear that shows the device 40 is in use. A ready light 48 (such as a green light) can be provided along with a sound (such as a bell ding) that activates when an item is ready to eat or drink, and these can be delayed for any amount of time that an item needs to rest before ready. The patient can retrieve the item from the preparation chamber 50 (by access through a door/screen). The interface screen 44 can prompt a response from the patient (such as accept/check) to report that the item is prepared and this can be electronically communicated to the patient mobile application 12 to update patient daily intake information. In the event that the item was not eaten and a new selection was prepared, that information can also be reported to the patient mobile application 12, and an alert can be sent to the dietitian application (dietitian's software 16). If the cycle continues, the dietitian can contact the patient as a follow-up to address prevailing concerns.

Multiple styles of food sources can be created with the kitchen device 40 because it has a high pressure/low pressure hot water infusion to cook and hydrate the ingredients, it also has multiple accessories for different applications of preparation such as a blender for smoothies. Cold item accessories snap into the base for preparation, when they snap out the container converts into a to-go drink container. Hot items pour directly into a mug or soup bowl of the user's choice that fits the specified size recommendations.

All the food items sold with the kitchen device 40 are single items only per cartridge 52 and not a combination of premixed ingredients; the meals are all based on menu created by a nutrition scientists that offer high quality, high nutrient, fresh meals, and drinks. Users can add fresh ingredients to the blended drinks if desired, and the interface allows for fresh ingredients to be added to their menu/recipe as an add-an-item. If the item added is not recommended the system can alert the patient/user prior starting the blender. A user can select the override option and the tracking system will recalculate additional item(s) into the daily meal plan. The system will not override and start the blender if the add-an-item is not recognized to protect patients/user with food allergies and food sensitivity from possible harm.

If multiple meals are made one after another or multiple times within a short amount of time, the kitchen device 40 can alert the dietitian's software 16 that there could be a possible problem and prompt the dietitian to take action, or make a follow up call to discuss the problem. If a patient is having trouble eating, and the caregiver is making multiple meals to accommodate the patient then this could escalade into a more serious condition, this gives the dietitian a chance to intervene more quickly with a resolution.

Problems from existing systems are that they do not address dietary consulting services, food management, and food preparation (cooking), and food accessibility all under one umbrella in a way that addresses disease associated malnutrition (DAM) from a cause and cure platform. Long-term deficiencies and poor nutritional habits are a root cause of disease and chronic illness and balanced nutrition rich diets are the cure.

Figure 6:
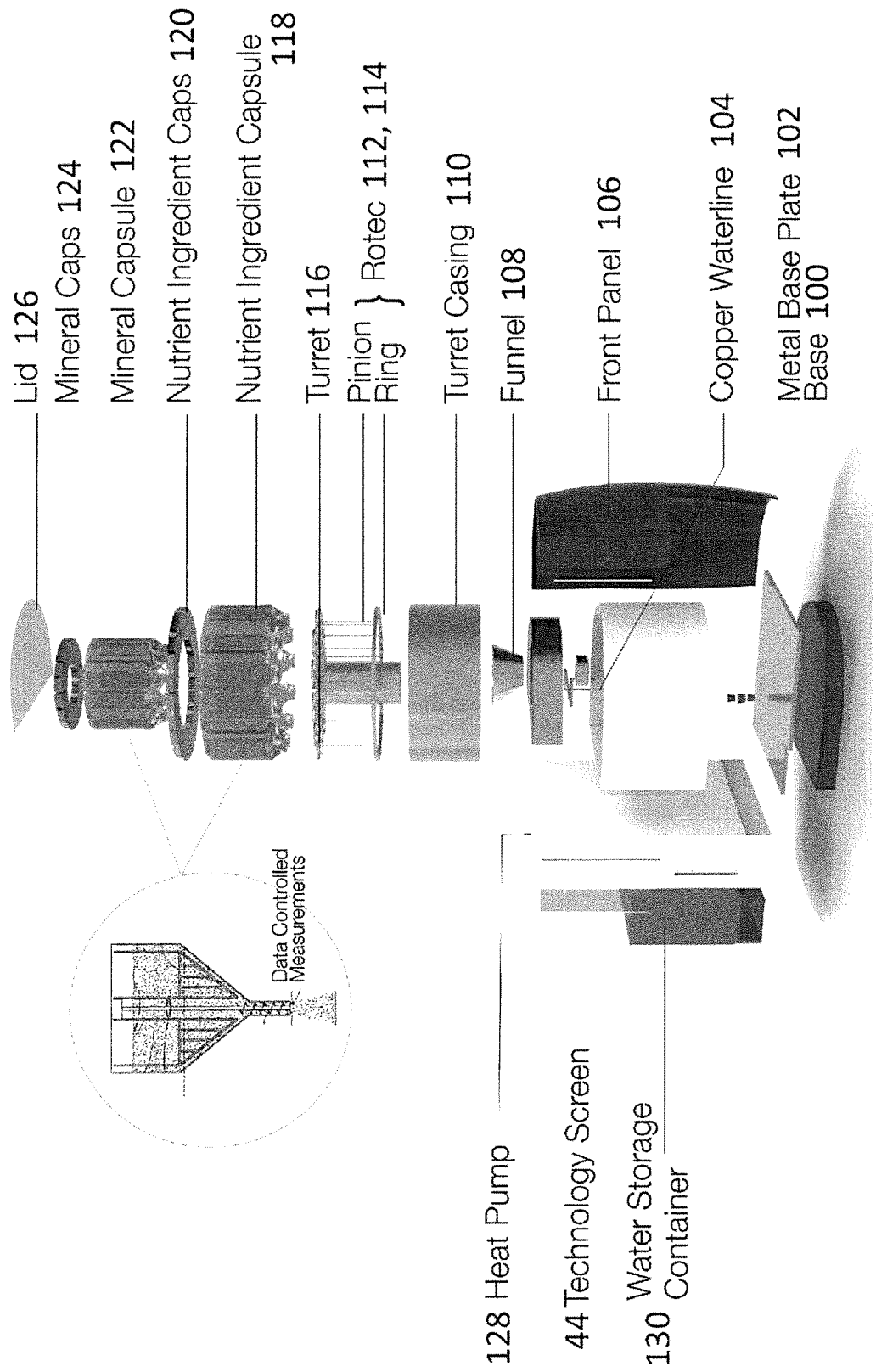
FIG. 6 is an exploded view of a kitchen device.
Figure 7A:
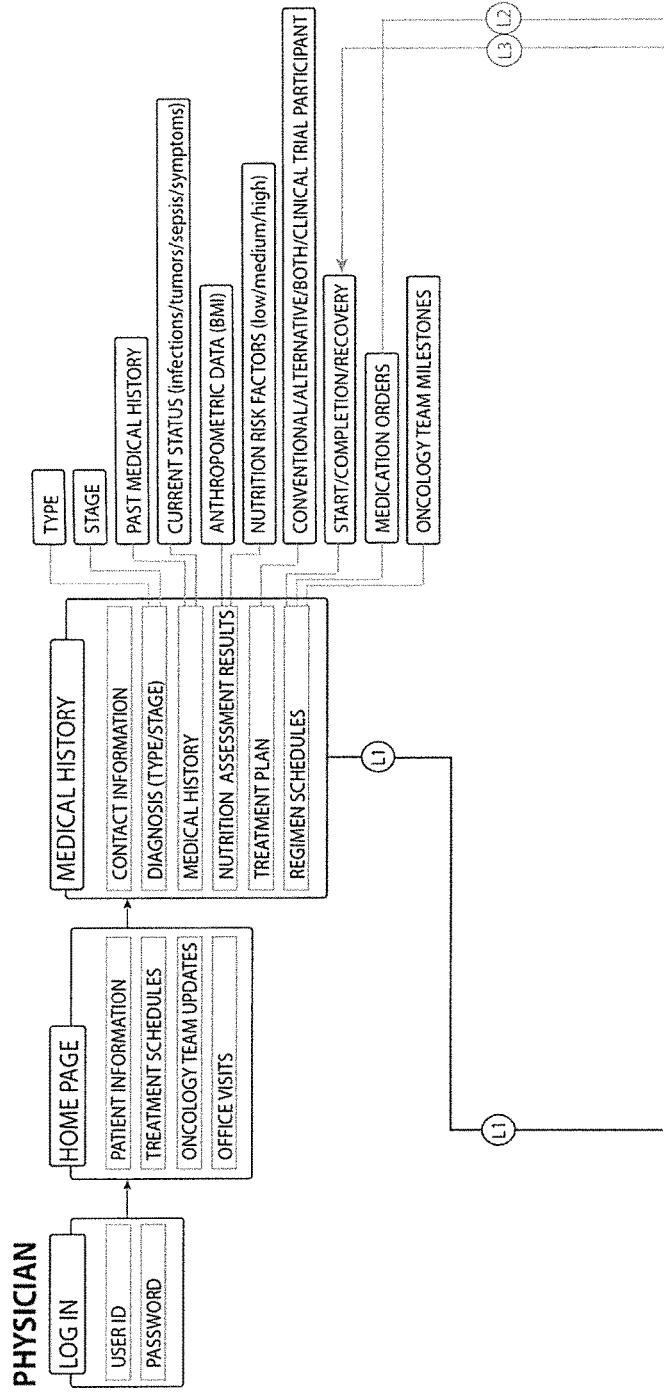
Figure 7B:
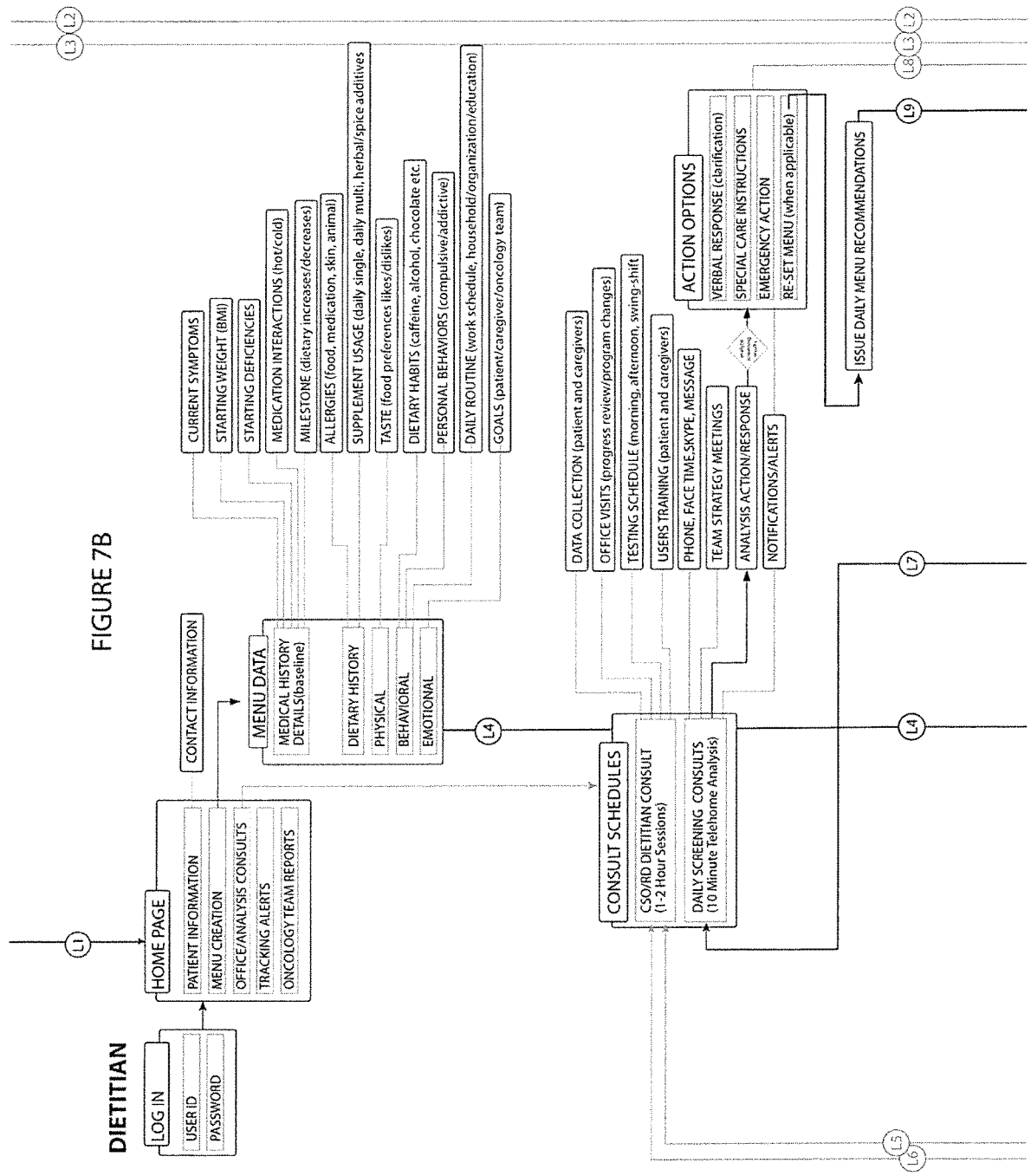
Figure 7C:
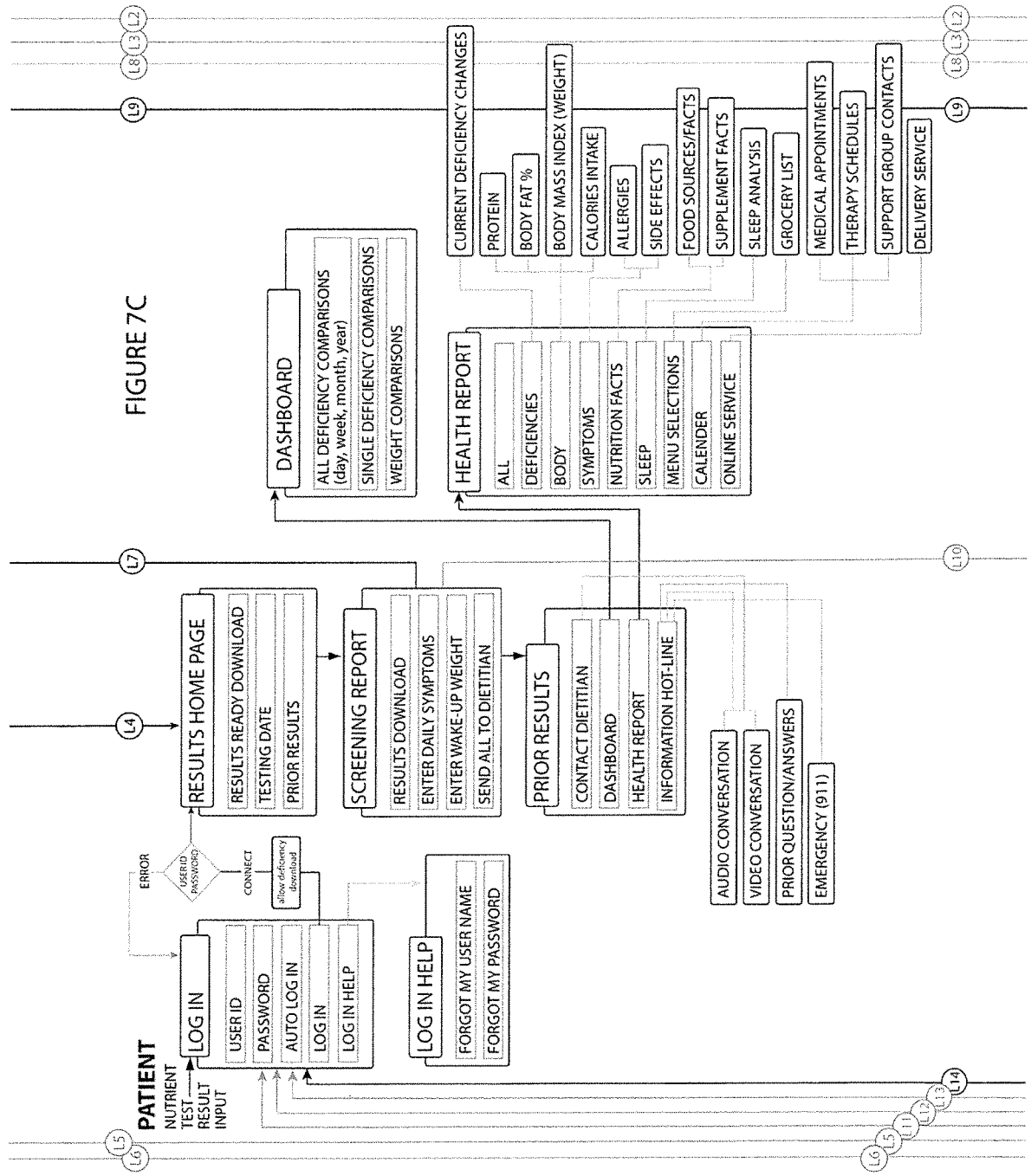

FIG. 6 details the internal mechanisms of the kitchen device 40 and can include a base 100, metal base plate 102, copper waterline 104, front panel 106, funnel 108, turret casing 110, rotec having a ring 112 and pinion 114, turret 116, nutritional ingredient capsule 118 for holding the cartridges 52, nutrient ingredient caps 120, mineral capsule 122, mineral caps 124, lid 126, heat pump 128, interface screen 44, and water storage container 130. Each of these items can be in operable connection and electronic connection where necessary.

The present invention therefore also provides for a method of using the kitchen device 40 by communicating with a patient mobile application 12 and determining available items, a patient selecting an available item, and preparing the item within a preparation chamber 50.

There are several benefits to the system 10. The system 10 provides accurate daily nutrient testing that is necessary because nutrients change daily in the body, as well as nearly instant testing results, available within minutes via mobile technology, so results can be more quickly utilized for menu planning. The system 10 automatically tracks testing results to the healthcare provider for daily analysis. The system 10 provides dietary recommendations based on daily-analyzed screening results provided by a registered dietitian to simplify dietary choices. The system 10 provides personalized dietary assistance and can identify potential problems, such as multiple selections made in odd durations of time, indicates the patient may not be eating properly. In these situation the healthcare provided will be alerted in order to aid in early engagement. All of these benefits, in conjunction will daily participation and generated dialog, lead to increased patient compliance.

When an institution provides recommendations of any kind, there is always a concern about protecting patients from bodily harm, as well as protecting their personal information. This is why the system 10 was designed to include many face-to-face consults between dietitians and patients/caregivers. Patient trust is essential for their continued compliance with the program. Building a strong dialog between all users will keep patients aware of potential risks and dangers of malnutrition due to starvation or mal absorption. The hotline information network is intended to offer patients another alternative to calling/contacting their healthcare provider directly to ask general questions about their nutrition program or report an emergency such as a food allergy. If their dietitians are unavailable, and it provides the institution yet another means to keep liability risks low.

This system 10 was created with the understanding that patients are unlikely to change all their negative habits, and instead it is unique in that it accounts for these habits in the analysis process. In their initial consults with dietitians, patients are encouraged to report their personal preferences, routines and positive/negative habits. Doing so will eliminate confusion for the dietitians when analyzing daily patient symptoms. It's important to note that some negative habits can change recommendations; for example, a man who smokes requires 34 mg more vitamin C than an individual who doesn't smoke. Taking these habits and behaviors into consideration offers dietitians the ability to tailor the system 10 to work around each patient's unique circumstances.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of nutrition management, including the steps of:
   a patient testing their nutrition levels on a home nutrient-testing device of a portable nano-scale microscope that measures nutrient levels in the patient daily;
   the home nutrient-testing device sending nutrient levels to a patient's mobile application on a patient mobile device;
   sending results of the home nutrient-testing device from the patient's mobile device to a dietitian's software on a dietitian mobile device;
   creating personalized daily dietary recommendations on a meal-by-meal basis for the patient based on results from the home nutrient-testing device with the dietitian's software and sending the personalized daily dietary recommendations to the patient mobile device; and
   the patient eating meals based on the recommendations and providing metabolic recovery to the patient.

2. The method of claim 1, wherein said creating step is further defined as a dietitian reviewing the patient's results, the dietitian creating personalized daily dietary recommendations.

3. The method of claim 2, wherein the personalized daily dietary recommendations include menus, recipes, and supplements.

4. The method of claim 1, further including the steps of the patient inputting daily symptoms and weight in the patient mobile application.

5. The method of claim 4, further including the step of the patient mobile application sending the results and patient inputs to the dietitian's software.

6. The method of claim 1, further including, before said creating step, the step of a dietitian creating a set of menus unique to the patient.

7. The method of claim 1, wherein said method is performed immediately after a patient's diagnosis of disease.

8. The method of claim 1, wherein said method is performed daily.

9. The method of claim 1, further including the step of the patient selecting a menu for a meal based on their schedule.

10. The method of claim 9, further including the step of selecting a meal based on a length of preparation time chosen from the group consisting of 5-minute grab-and-go and 10-20 minute home cook.

11. The method of claim 9, further including selecting a meal from an order-out healthy restaurant locator.

12. The method of claim 9, further including the step of tracking the patient's menu selections.

13. The method of claim 12, further including the step of updating recommendations in real time based on the patient's previous menu selections to provide the patient with needed nutrients.

* * * * *